United States Patent
Gu et al.

(10) Patent No.: US 7,989,211 B1
(45) Date of Patent: Aug. 2, 2011

(54) FUNCTIONALIZED GOLD SURFACE-ENHANCED RAMAN SCATTERING SUBSTRATE FOR RAPID AND ULTRA-SENSITIVE DETECTION OF ANIONIC SPECIES IN THE ENVIRONMENT

(75) Inventors: Baohua Gu, Oak Ridge, TN (US); Chuanmin Ruan, Oak Ridge, TN (US); Wei Wang, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 12/645,017

(22) Filed: Dec. 22, 2009

Related U.S. Application Data (62) Division of application No. 11/528,016, filed on Sep. 27, 2006, now abandoned.

(51) Int. Cl.
*G01N 33/00* (2006.01)
*G01N 21/65* (2006.01)

(52) U.S. Cl. ........ 436/101; 436/110; 436/124; 436/125; 436/164; 436/171; 436/172

(58) Field of Classification Search .............. 422/56–58, 422/61, 82.05; 436/57, 82, 101, 124–125, 436/110, 164, 171–172
See application file for complete search history.

(56) References Cited

U.S. PATENT DOCUMENTS

| | | | |
|---|---|---|---|
| 6,221,673 B1 * | 4/2001 | Snow et al. | 436/149 |
| 2003/0077625 A1 * | 4/2003 | Hutchison | 435/6 |
| 2005/0142030 A1 * | 6/2005 | Kim et al. | 422/58 |

OTHER PUBLICATIONS

Okahata, Y. et al, Supramolecular Science 1996, 3, 165-169.*
Evans, S. D. et al, Journal of Materials Chemistry 2000, 10, 183-188.*
Warner, M. G. et al, Chemistry of Materials 2000, 12, 3316-3320.*
Woehrle, G. et al, Journal of Physical Chemistry B 2002, 106, 9979-9981.*
Mosier-Boss, P. A. et al, Applied Spectroscopy 2003, 57, 1129-1137.*
Gu, B. et al, Applied Spectroscopy 2004, 58, 741-744.*
Woehrle, G. et al, Inorganic Chemistry 2005 44 6149-6158.*
Science Direct; Development of Gold-silica composite nanoparticle substrates for perchlorate detection by surface-enhanced Raman spectroscopy; Feb. 28, 2006 pp. 121-126; Wang, et al.

(Continued)

*Primary Examiner* — Arlen Soderquist
(74) *Attorney, Agent, or Firm* — Sara C. Kanos; Nexsen Pruet, LLC

(57) ABSTRACT

This invention relates to the development of a new Raman enhancing reagent and a surface-enhanced Raman scattering (SERS) method for rapid and ultra-sensitive detection and identification of perchlorate ($ClO_4^-$) and other anions such as technetium ($TcO_4^-$), uranium and nitrate in environmental samples. The method involves the synthesis of controlled gold nanoparticles which are modified with amine functional groups such as 2-(dimethylamino)ethanethiol and N,N,N-trimethylaminethiol. These functionalized Au nanoparticles were found to be reactive with perchlorate and other anions and can be used to detect these anions by Raman spectroscopy at ultra low concentrations in complex environmental matrices. This invention overcomes the limitations of currently-available analytical techniques by offering an inexpensive, rapid, ultra-sensitive, and real-time identification and detection of perchlorate and other anions. The technique is not only sensitive but also highly specific because of the unique Raman vibrational bands of perchlorate and other anions.

1 Claim, 8 Drawing Sheets

OTHER PUBLICATIONS

Science Direct; Surface-enhanced Raman scattering for perchlorate dectection using cystamine-modified gold nanoparticles; Mar. 9, 2006; pp. 114-120; Ruan, et al.

Applied Spectroscopy; vol. 59, No. 12, 2005; New Surface-Enhanced Raman Spectroscopy Substrates via Self-Assembly of Silver Nanoparticles for Perchlorate Detection in Water; Wang et al.

* cited by examiner

FUNCTIONALIZED GOLD SURFACE-ENHANCED RAMAN SCATTERING SUBSTRATE FOR RAPID AND ULTRA-SENSITIVE DETECTION OF ANIONIC SPECIES IN THE ENVIRONMENT

CROSS-REFERENCE TO RELATED APPLICATIONS

The present application is a divisional application of U.S. patent application Ser. No. 11/528,016 filed Sep. 27, 2006, which is now abandoned.

STATEMENT REGARDING FEDERALLY SPONSORED RESEARCH OR DEVELOPMENT

Not applicable.

REFERENCE TO A SEQUENCE LISTING, A TABLE, OR A COMPUTER PROGRAM LISTING COMPACT DISC APPENDIX

Not Applicable.

BACKGROUND OF THE INVENTION

The present invention is directed to a functionalized metal substrate and method for detection of anions of concern in environmental samples.

Perchlorate ($ClO_4^-$) has been detected recently in groundwater, surface water, and soils and, more ominously, in plants, food products and human breast milk in many areas of the United States and the world. Most perchlorate is manufactured for use as a primary ingredient of solid rocket propellant and explosives. However, perchlorate is also used in pyrotechnic devices, such as fireworks, highway flares, gun powder, air bags, and in a wide variety of industrial applications such as tanning and leather finishing, rubber manufacturing, and paint and enamel production. Naturally-occurring perchlorate is also known to exist. As a result, the widespread use and the presence of both natural and anthropogenic perchlorate have caused widespread contamination in groundwater and drinking water supplies. For example, the entire Lake Mead and the lower Colorado River are contaminated with perchlorate, affecting millions of people and agricultural lands. Because of its potential health affect on thyroid function and hormone production by interfering with iodide uptake, the widespread occurrence of perchlorate in the environment has resulted in intense public debate and far-reaching ramifications, ranging from public health issues to liabilities that could be imposed by environmental cleanup needs.

Perchlorate is also exceedingly mobile in aqueous systems and can persist for many decades under typical groundwater and surface water conditions. Many states have already set regulatory or advisory levels of perchlorate in drinking water, ranging from 1 to 18 µg/L (e.g., 1 µg/L in Maryland, Massachusetts, and New Mexico, and 6 µg/L in California). Therefore, methods for a rapid and sensitive assay of this contaminant are urgently needed to allow continuous monitoring and detection of this contaminant in groundwater and drinking water. At present, ion chromatography (IC) with conductivity detection is the recommended method by EPA for quantitative analysis of perchlorate. Its detection of perchlorate is based on the retention-time when perchlorate is eluted off an IC column. Therefore, this method is not only non-selective but also requires a lengthy analytical time. IC has a detection limit of ~1 ppb for perchlorate in a relatively pure water analysis but exhibits problems for analysis in some environmental samples due to interferences from other dissolved ions or species in water. For example, in fertilizer analyses, the concentration of perchlorate is typically orders of magnitude less than that of other oxyanions (e.g., nitrate, sulfate, and phosphate) that are usually present in the fertilizer extracts. At high TDS (total dissolved solids) concentration, the IC peaks broaden due to column overloading to the extent of obscuring the less-prominent perchlorate peak. Even when the perchlorate peak is not completely obscured, tailing associated with column overload may add errors in peak area integration. In addition, the detector overload due to high TDS concentration may severely affect baseline response. Therefore, to successfully perform an analysis for perchlorate at a high TDS concentration, a tedious pretreatment including dilution, cleanup procedures is required. Such a pretreatment significantly increases the total time and labor required for analysis. Other problems that IC exhibits for analysis of perchlorate in complex matrices include retention time migration with column deterioration, detector fouling, and long data acquisition time. IC coupled with mass spectrometry (IC-MS) has also be used with a better sensitivity (~0.01 ug/L) but the analytical cost is enormous, and the analysis is also subjected to interferences by the presence of other ions and impurities in environmental samples For long-term monitoring, it is desirable to detect perchlorate ions in situ to minimize sample volume, handling time, and costs. Based on recent studies of the inventors, an effective method for rapid, sensitive, and in situ detection of $ClO_4^-$, as well as other anionic contaminants including radioactive technetium and uranium, can include surface-enhanced Raman scattering (SERS) analysis. Portable Raman spectrometer systems coupled with fiber-optic probes are now commercially available and are relatively inexpensive, robust, and require only minimal sample preparation and handling. The characteristic vibration frequency of the symmetric stretch for $ClO_4^-$ at ~950 $cm^{-1}$ (dehydrated) and ~934 $cm^{-1}$ (in aqueous solution) makes the technique especially selective. Using unfunctionalized silver nanoparticles as substrates, we recently reported a detection limit of 100 µg/L by SERS. An even lower detection limit (~10 µg/L) was achieved by first concentrating $ClO_4^-$ onto a bifunctional anion-exchange resin followed by the normal Raman spectroscopic detection.

Accordingly, there exists a need for sensitive and stable SERS substrate materials in order to enhance the detection limit of perchlorate and other anionic chemical species in the environment.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

The present invention includes a SERS substrate or reagent (i.e., herein referred to as a substrate or reagent capable of causing surface enhanced Raman scattering) and method for using this reagent for rapid, sensitive, selective, and quantitative analysis of target analytes in environmental samples with greatly reduced analytical time and costs. In particular, the SERS reagent includes metal nanoparticles that are modified with a functional group that can provide a positive charge to the surface of the nanoparticles. For example, the metal can be gold (Au) and the functional group can be an amine, such as 2-(dimethylamino)ethanethiol. This reagent can be added to samples of interest, which are thereafter subjected to a SERS analysis for the detection various target analytes. Such target analytes can include perchlorate and radionuclides, such as Technetium-99 (Tc) and Uranium (U).

A feature of the present invention includes the use of a reagent including metal nanoparticles modified by functional groups that provide a positive charge to the surface of the nanoparticles. This reagent can effective at detecting the presence and quantity of certain ions of interest, including perchlorate, nitrate, technetium (as pertechnetate) and uranium (as uranyl carbonate or other anionic complexes).

Another feature of the present invention includes the use of SERS to analyze a sample having a reagent that includes gold nanoparticles modified by functional groups that provide a positive charge to the surface of the nanoparticles. This combination provides a relatively simple and inexpensive way of performing rapid, sensitive, selective, and quantitative analysis of perchlorate, nitrate, and radioactive materials, including technetium and uranium. Significantly, a detection limit of perchlorate as low as $10^{-10}$ M (or 0.01 ppb) was achieved by using this new SERS reagent. This is 3 orders of magnitude lower than the lower detection limit (LOD) reported previously using Raman spectroscopy. Furthermore, the technique could be readily adapted for in situ, real-time monitoring of target analytes in the environment when coupled with fiber optic, hand-held Raman systems.

These and other features and their advantages will be apparent to those skilled in the art from a careful reading of the Detailed Description of Preferred Embodiments, accompanied by the following drawings.

DETAILED DESCRIPTION OF PREFERRED EMBODIMENTS

Referring now to the following detailed information, and to incorporated materials; a detailed description of the invention, including specific embodiments, is presented.

Unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contains certain errors necessarily resulting from the standard deviation found in their respective testing measurements.

General Description:

The present invention provides a novel SERS substrate or reagent and method for using this reagent for rapid, sensitive, selective, and quantitative analysis of target analytes in aqueous solutions through the use of surface-enhanced Raman scattering (SERS) analysis. The reagent generally includes a metal nanoparticle that has been modified by a functional group, which provides a positive charge to the surface of the metal nanoparticle. As used herein, "modified" references to a chemical linked by a bond, whether such bond is covalent or ionic. "Functional group" as used herein includes a group of chemical substituents sharing characteristic properties. By utilizing such designed nanoparticles, the present invention can determine that presence of one or more target anayltes (i.e., herein meaning an element or molecule the characteristics of which are of concern in a particular sample).

Figure 1:
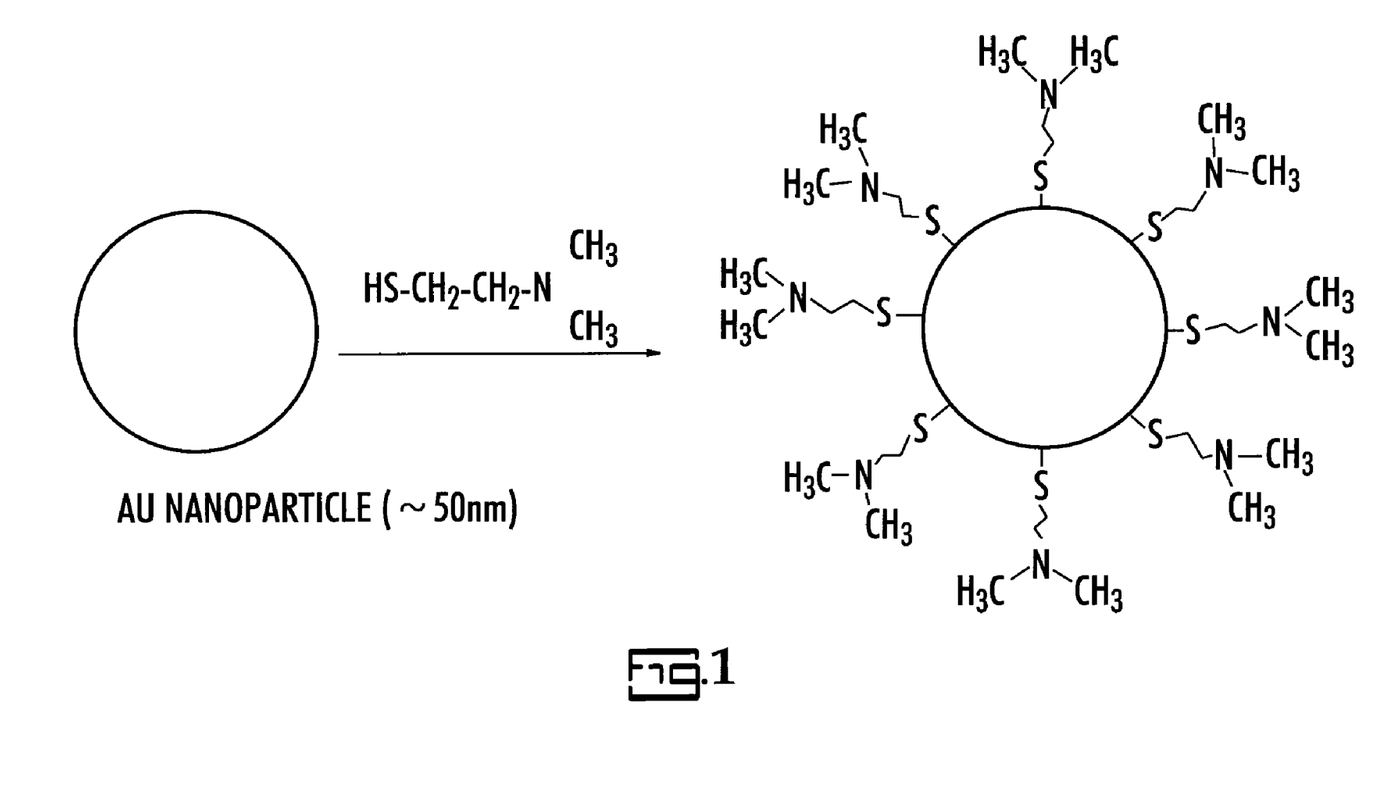
FIG. 1 illustrates a simplified schematic view of the synthesis of a SERS reagent according to an embodiment of the present invention.

Specific Description:

Turning now to the drawings, FIG. 1 shows a schematic view of a SERS reagent according to a preferred embodiment of the present invention. In particular, the metal nanoparticle is colloidal gold. This gold nanoparticle is modified with a functional group that provides a positive charge to the surface of the Au nanoparticle. A functional group that has provided positive results with the present invention is an amine- or quaternary amine-containing functional group such as dimethylamino-ethanethiol and N,N,N-trimethylaminethiol. The particular amine functional group shown in FIG. 1 is 2-(dimethylamino)ethanethiol.

The SERS reagent shown in FIG. 1 can be prepared in many different ways. The following is a non-limiting illustration of this particular embodiment of the present invention.

Synthesis of Au Nanoparticles Modified by 2-(dimethylamino)ethanethiol

"Seed" colloidal suspension of gold was first prepared by reduction of $HAuCl_4.3H_2O$ in aqueous solution in the presence of 0.075% $NaBH_4$ in 1% trisodium citrate and then stored at 4° C. until use. Colloidal Au nanoparticles (~50 nm diameter) were prepared by heating 2 mL of 1% $HAuCl_4.3H_2O$ in 450 mL of deionized water to boiling, followed by the addition of 500 μl of above "seed" colloids and 1.8 ml of a 1% trisodium citrate solution. The solution mixture was refluxed for an additional 10 min before it was cooled under agitation.

Figure 2:
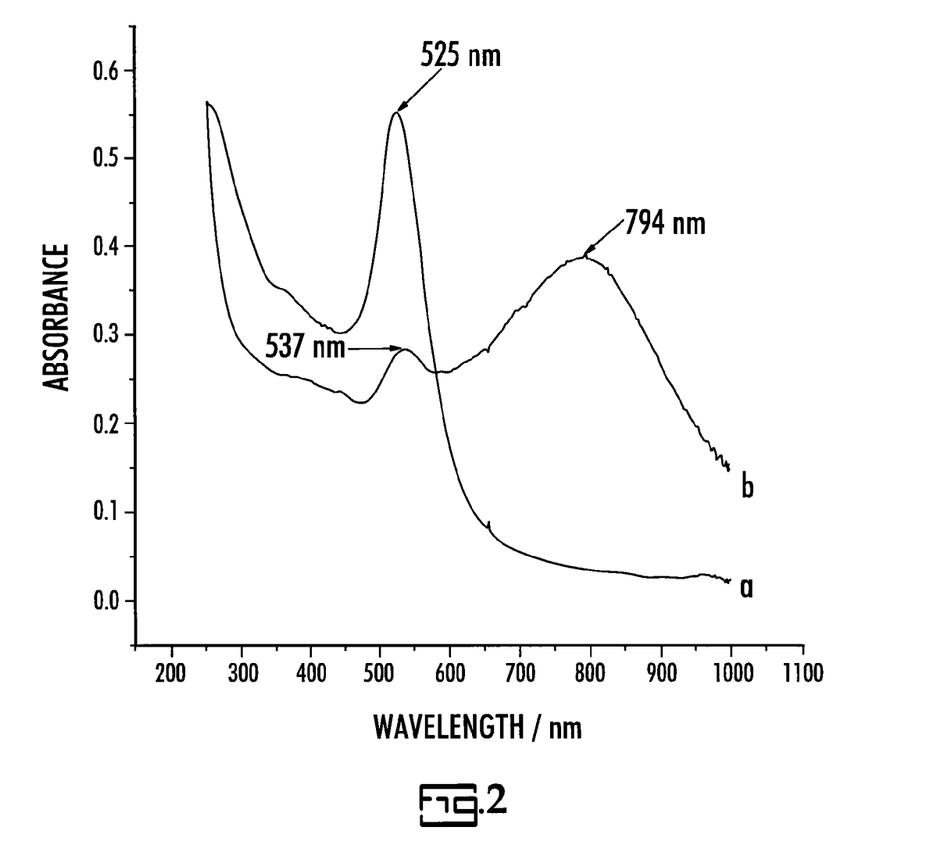
FIG. 2 shows UV-visible spectra of gold nanoparticles of the present invention compared to other nanoparticles.

A major discovery and feature of this invention is that gold nanoparticles, when modified with amine functional groups such as 2-(dimethylamino)ethanethiol, were found to be highly reactive with perchlorate and to give an extremely strong enhancement in SERS signal for perchlorate. Additionally, the same reagent could be used for sensitive detection of other anions such as radioactive technetium (as $TcO_4^-$), uranium and nitrate. The process and structure of the modification reaction of Au was illustrated in FIG. 1. The modification was performed by adding about 0.3 g of 2-(dimethylamino)ethanethiol into 400 mL of the above prepared colloid Au solution. The color of colloidal Au immediately changed from red to deep purple upon the addition of 2-(dimethylamino)ethanethiol. The UV-visible absorption spectra of bare and modified gold colloids in solution are shown in FIG. 2. After reaction for approximate 5 h, the solution was centrifuged at 14000 rpm, and the supernatant was discharged. The concentrated, 2-(dimethylamino)ethanethiol-modified Au nanoparticles were then washed, re-suspended in 0.01 M HCl solution, and used as SERS substrate reagent for the detection of perchlorate and other anionic chemical species.

Figure 3:
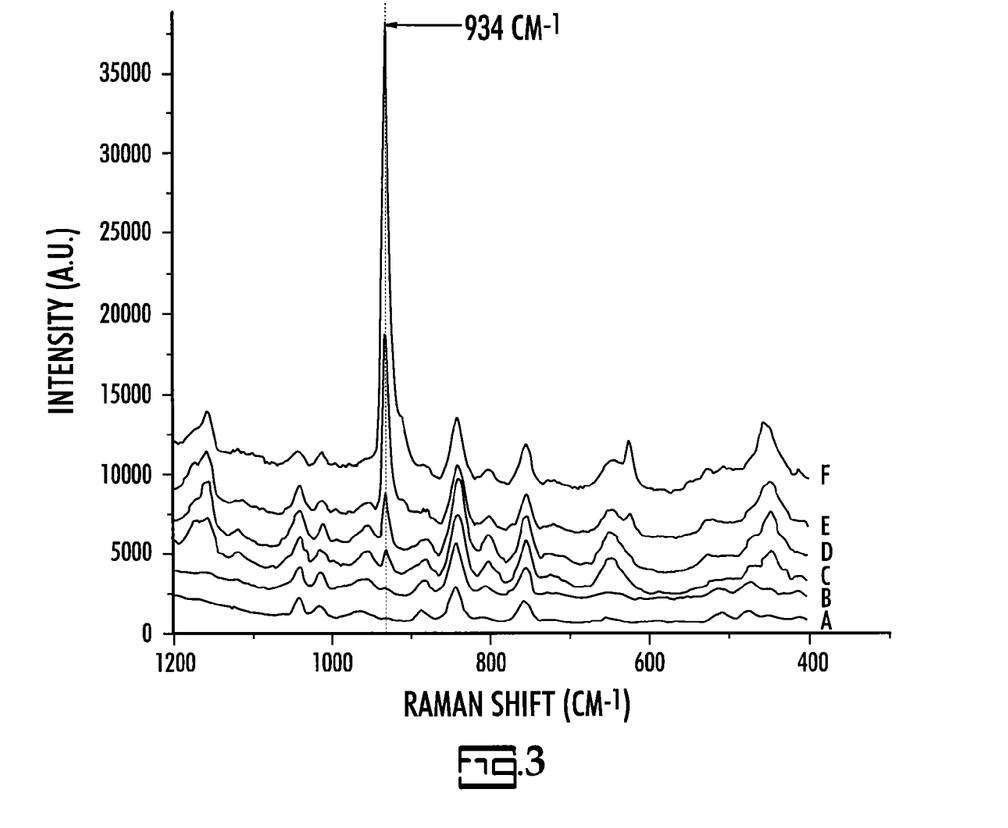
FIG. 3 shows SERS detection of perchlorate in aqueous solution by using surface functionalized Au nanoparticles of the present invention.
Figure 4:
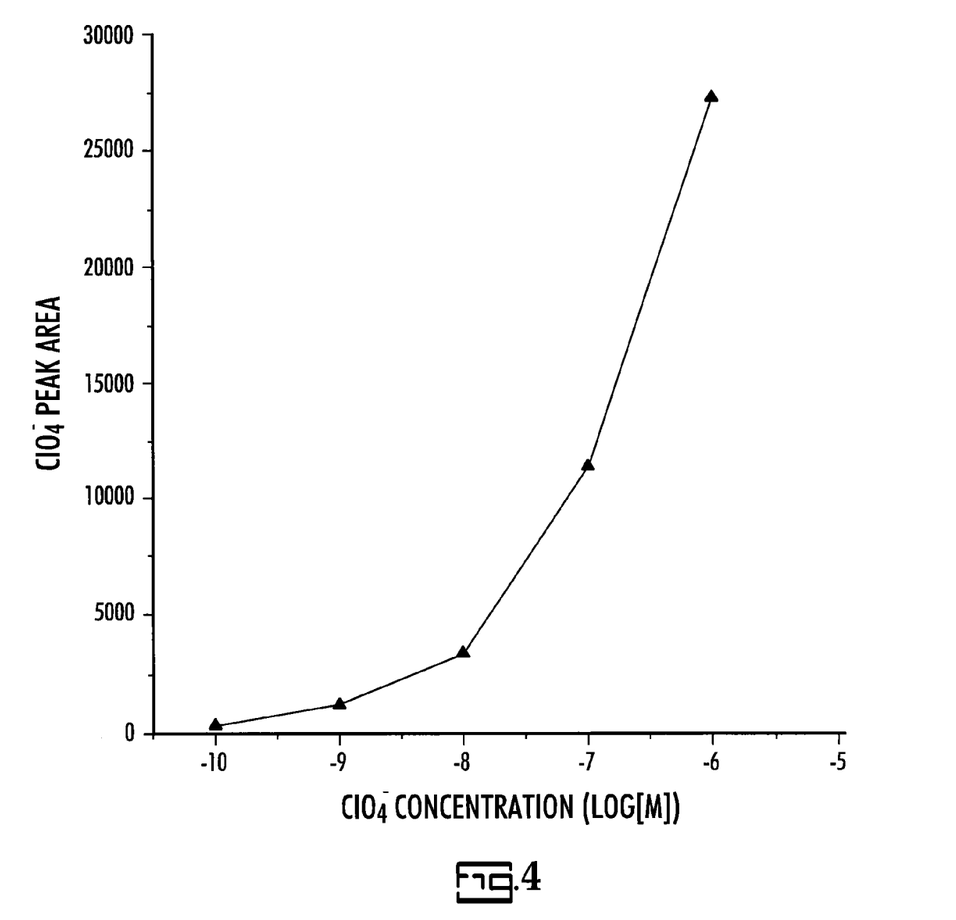
FIG. 4 shows a perchlorate peak area plot as a function of perchlorate concentration in water analyzed by using the reagent of the present invention.
Figure 5:
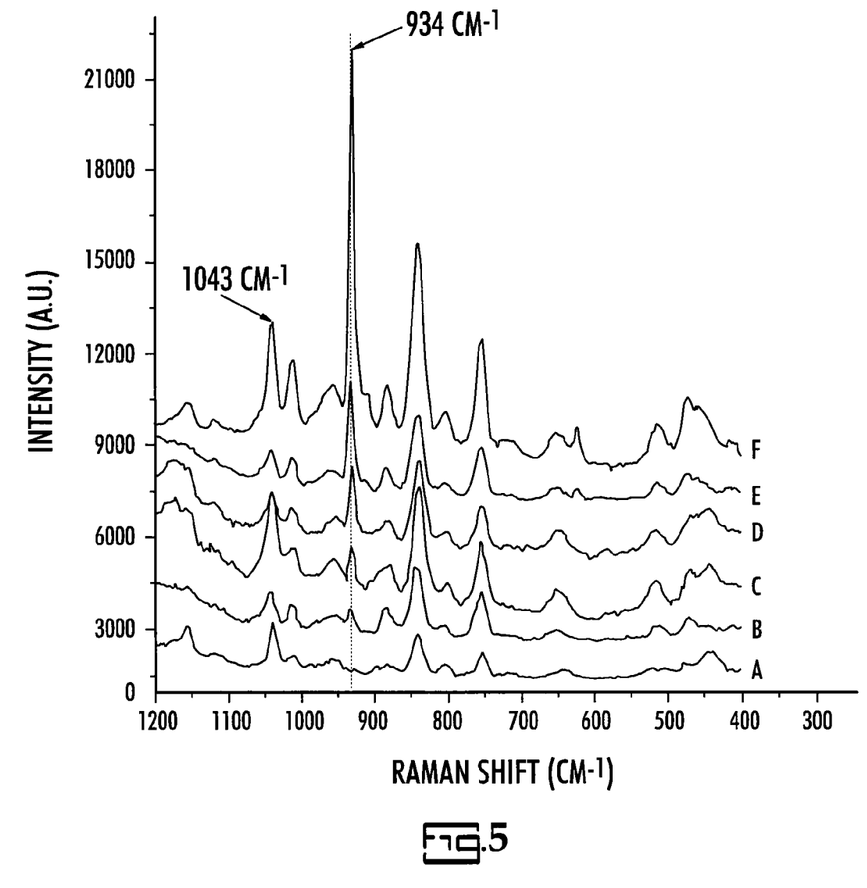
FIG. 5 shows SERS detection of perchlorate in aqueous solution in the presence of interfering anions such as $NO_3^-$, $SO_4^-$, $PO_4^-$, and $Cl^-$ by using the reagent of the present invention.

Raman spectra were obtained through the Renishaw micro-Raman system equipped with a 300 mW near infrared diode laser at a wavelength of 785 nm for excitation (Renishaw Inc, New Mills, UK). The laser beam was set in position through a Leica Raman Imaging Microscope objective (50×) at a lateral spatial resolution of ~2 μm. A charge-coupled device (CCD) array detector was used to achieve signal detection from a 1200 grooves/mm grating light path controlled by Renishaw WIRE software and analyzed by Galactic GRAMS software. SERS solutions were prepared by mixing 100 μL 0.1 M HCl solution containing modified Au nanoparticles, 100 μL diluted perchlorate solution (or other anions) in the concentration range of $1 \times 10^{-6}$ to $1 \times 10^{-10}$ M, (100 ppb to 0.01 ppb) and 800 μL of water. The final pH of the working solution is pH 3. The background control solution was prepared similarly without the addition of the perchlorate solution. SERS substrate samples were prepared by casting one drop (~10 μL) of the mixed solution of perchlorate and Au nanoparticles on a glass slide. Raman spectra were then collected Determination of Perchlorate in Pure Water Sample FIG. 3 shows SERS spectra at different concentrations of perchlorate in pure water samples. Results clearly indicate that that there is no background peaks for modified Au nanoparticles in the Raman shift ranging from 960 to 858 cm$^{-1}$ (curve a), indicating no interferences from SERS substrate itself. The characteristic Raman shift for perchlorate in solution appeared at 934 cm$^{-1}$ for other samples containing perchlorate. A clear Raman peak at 934 cm$^{-1}$ was observed at concentrations as low as $10^{-10}$ M (0.01 ppb) of perchlorate. This represents the lower detection limit (LOD) and is the lowest LOD reported to date for the detection of perchlorate. This LOD is more than 3 orders of magnitude lower than previously reported LODs by Raman spectroscopy. FIG. 3 also indicates that the Raman peak height at Raman shift of 934 cm$^{-1}$ increased with concentrations of perchlorate in the samples, further proving that the invented method can be used for quantification of perchlorate in aqueous samples. FIG. 4 shows integrated peak areas as a function of perchlorate concentration in water. Note that the X-axis is on log-scale, representing 5 orders of magnitude differences in concentration Determination of Perchlorate in Simulated and Contaminated Environmental Samples Environmental samples generally contain many kinds of anions, especially oxyanions such as nitrate, sulfate, phosphate anions. Their effects on Raman response with modified Au nanoparticles were examined. FIG. 5 shows SERS spectra obtained with different concentrations of perchlorate ($10^{-6}$ to $10^{-10}$ M) in a mixed solution containing 0.1 mM of $SO_4^{2-}$, $PO_4^{3-}$, $NO_3^-$ and 1 mM of Cl$^-$ at pH 3.0. Results indicate that sulfate, phosphate and chloride anions do not interfere with the detection of perchlorate, and no Raman bands were observed for these anions within 1200 to 400 cm$^{-1}$ and at a concentration of $10^{-4}$ M. Although nitrate gives a SERS band at ~1043 cm$^{-1}$, it is sufficiently separated from the perchlorate band (at ~934 cm$^{-1}$) and thus did not interfere with the analysis of perchlorate either. Additionally, this SERS peak may also be used for the determination of nitrate ions simultaneously with perchlorate. The detection limit for nitrate was found to be ~$10^{-6}$ M due to a background peak of the reagent at ~1043 cm$^{-1}$.

Figure 6:
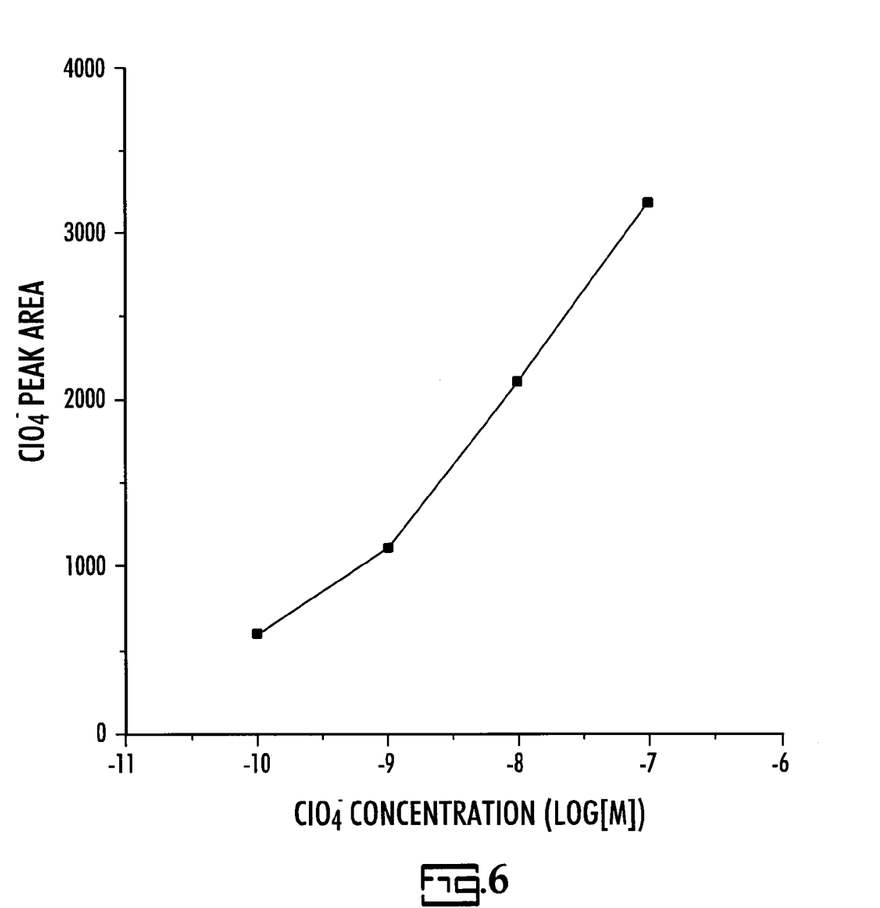
FIG. 6 shows a perchlorate peak area plot as a function of perchlorate in a mixture solution containing $NO_3^-$, $SO_4^-$, $PO_4^-$, and $Cl^-$ (shown in FIG. 5).

Despite the presence of these interfering ions, a detection limit of $10^{-10}$ M for perchlorate was also achieved in these simulated environmental samples (FIG. 5). The peak area at 934 cm$^{-1}$ as a function of the perchlorate concentration is also shown in FIG. 6. At perchlorate concentrations from $10^{-7}$ to $10^{-10}$ M (10 to 0.01 ppb), the peak area increased with the perchlorate concentration, again suggesting that the technique could be used for quantitative determination of perchlorate in environmental samples. Significantly, although nitrate does not interfere with the perchlorate detection, the presence of perchlorate in solution appears to diminish the SERS response of nitrate anions, indicating the selective characteristics of our modified Au nanoparticles for perchlorate.

Figure 7:
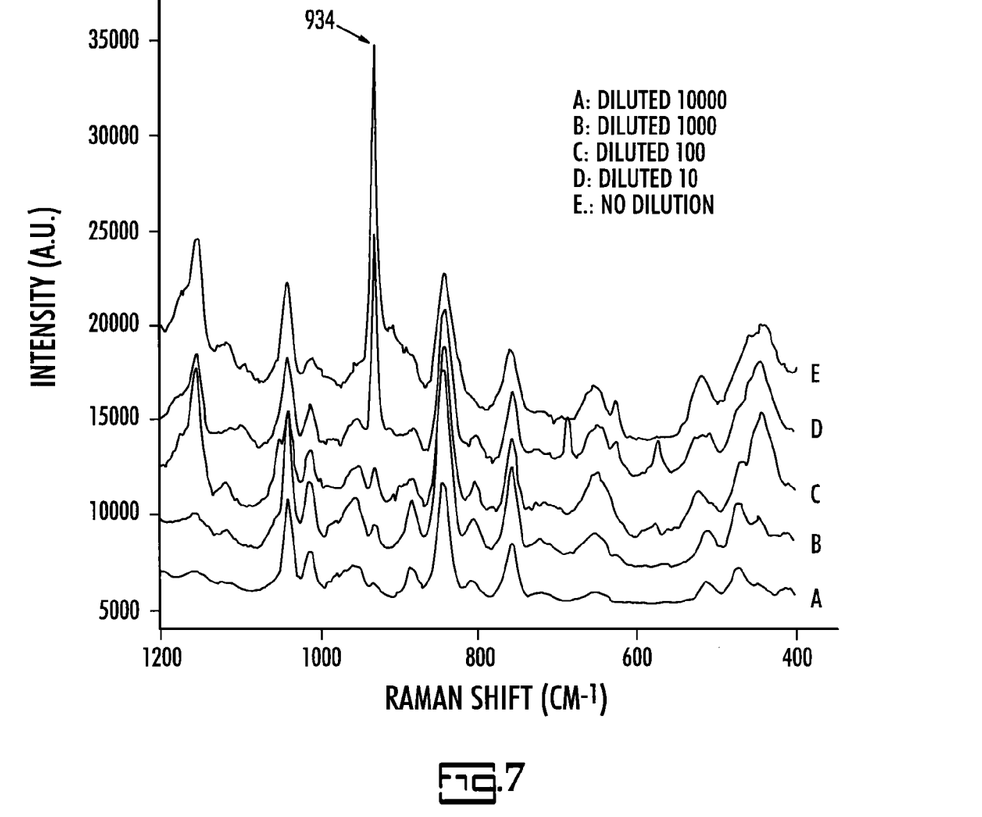
FIG. 7 shows SERS detection of perchlorate in a contaminated groundwater (from California) at various dilutions by using the nanoparticles of the present invention.

The SERS reagent of the present invention was also used for detecting perchlorate from a contaminated groundwater obtained from Northern California (initially provided as a blind sample from a third party). The groundwater contained a perchlorate concentration at about 835 ppb (analyzed by ion chromatography). Results (FIG. 7) indicate that this same technique with modified Au colloids is sensitive and capable of detecting perchlorate in realistic environmental samples. The perchlorate peak intensity (at 934 cm$^{-1}$) decreased consistently with an increase in dilution factors from 0 to 10,000.

The present invention further contemplates the detection of target analytes in addition to perchlorate and nitrate. The following is another non-limiting illustration of the specific embodiment of the present invention.

Determination of Pertechnetate and Other Anions

Figure 8:
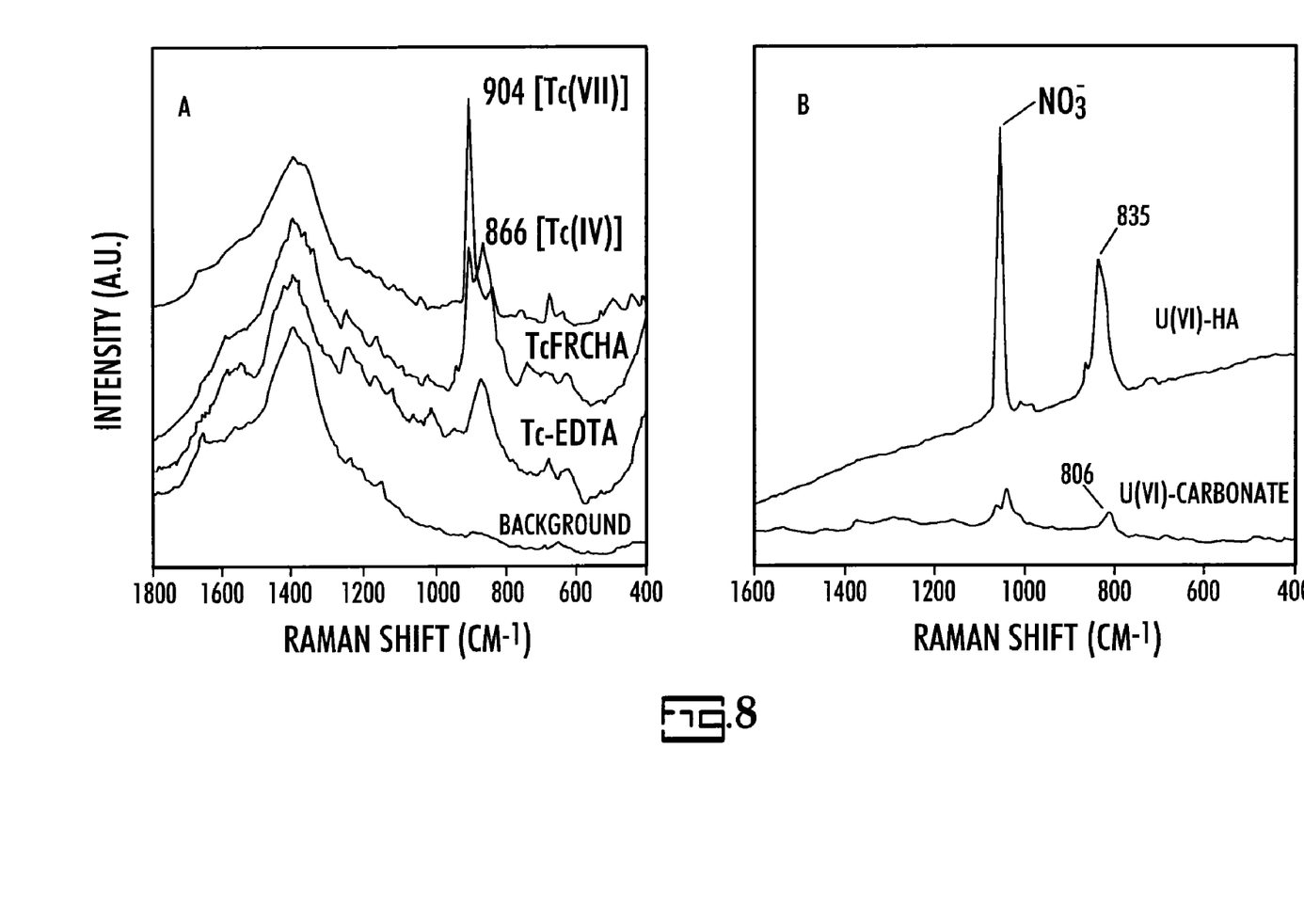
FIG. 8 shows SERS detection of Technetium and Uranium in aqueous solution by using nanoparticles of the present invention.

Both Technetium-99 ($^{99}$Tc) and Uranium ($^{238}$U) are radioactive materials of concern and have been found at a number of US Department of Energy (DOE) and other industrial contaminated sites. They pose great environmental and ecological risks because of their radioactivity and long half-lives. It was discovered that the new SERS reagent and method is equally applicable for the detection and analysis of these radionuclides at micro-molar concentration ranges (FIG. 8). In particular, the method is also capable of distinguishing different species of Tc and U. The oxidized Tc(VII) (as $TcO_4^-$) shows a distinct vibrational band at ~904 cm$^{-1}$ whereas reduced Tc(IV) exhibits a Raman shift at about 866 cm$^{-1}$ (FIG. 8a). The reduced Tc(IV) was also found to form complexes with various organic ligands such as humic acid (HA) and EDTA. Similarly, the new SERS method was found to be sensitive to detect U(VI) species, and a detection limit as low as 1 μM has been achieved by using the Au reagent of the present invention (FIG. 8b). More importantly, different species of U(VI) complexation with HA or carbonates can be distinguished by the SERS analysis. The complexation between U(VI) and bicarbonate resulted in a Raman shift at 806 cm$^{-1}$, whereas a Raman shift at 835 cm$^{-1}$ was observed for the complexation between uranyl and the humic acid. Additionally, nitrate ($NO_3^-$) is also detected in U(VI)-HA sample due to the use of $UO_2(NO_3)_2$ stock solution.

It is further contemplated by the present invention that additional embodiments employing different metal nanoparticles modified by different functional groups than those discussed in detail can be effective at rapid SERS detection of target analytes. In particular, the inventors make specific reference to the following publications, which are incorporated herein by reference: "New Surface-Enhanced Raman Spectroscopy Substrates via Self-Assembly of Silver Nanoparticles for Perchlorate Detection in Water" by Wei Wang and Baohua Gu, published in *Applied Spectroscopy*, Volume 59, Number 12, 2005; "Surface-enhanced Raman Scattering for Perchlorate Detection Using Cystamine-Modified Gold Nanoparticles" by Chuanmin Ruan, Wei Want, Baohua Gu, published in *Analytica Chimica Acta*, 567, 114-120, 2006; "Development of Gold-Silica Composite Nanoparticle Substrates for Perchlorate Detection by Surface-Enhanced Raman Spectroscopy" by Wei Wang, Chuanmin Ruan, Baohua Gu, published in *Analytica Chimica Acta*, 567, 121-126, 2006. These non-limiting examples provided consistent, but less positive results. In particular, it was shown that the use of gold rather than silver nanoparticles enhanced the SERS effect. Furthermore, it was shown that the use of 2-(dimethylamino)ethanethiol as the functional group provided enhanced results as compared to the use of cystamine as the functional group.

It will be apparent to those skilled in the art that many changes and substitutions can be made to the foregoing preferred embodiment and method without departing from the spirit and scope of the invention, which is defined by the appended claims.

What is claimed is:

1. A method for determining the presence or amount of perchlorate and nitrate in a test sample comprising:
    providing a test sample having an amount of perchlorate and including nitrate;
    adding a SERS reagent to said test sample, wherein said SERS reagent comprises:
    a metal nanoparticle having a surface; and
    a functional group, wherein said surface of said nanoparticle is modified by said wherein said surface is modified by said functional group, and wherein said functional group provides a positive charge to said surface;
    allowing said SERS reagent to bind to said perchlorate;
    measuring the intensity of the Raman scattering signal;
    determining the presence or amount of said perchlorate;
    allowing said SERS reagent to bind to said nitrate;
    measuring the intensity of the Raman scattering signal; and
    determining the presence or amount of said nitrate.

* * * * *